(12) United States Patent
Lilleberg et al.

(10) Patent No.: US 7,115,604 B2
(45) Date of Patent: Oct. 3, 2006

(54) METHOD FOR TREATING ERECTILE DYSFUNCTION

(75) Inventors: Jyrki Lilleberg, Sirkkalanmäki 32, Fin-00760, Helsinki (FI); Lasse Lehtonen, Espoo (FI); Pertti Pentikäinen, Helsinki (FI)

(73) Assignees: Orion Corporation, Espoo (FI); Jyrki Lilleberg, Helsinki (FI)

( * ) Notice: Subject to any disclaimer, the term of this patent is extended or adjusted under 35 U.S.C. 154(b) by 0 days.

(21) Appl. No.: 10/450,304

(22) PCT Filed: Dec. 14, 2001

(86) PCT No.: PCT/FI01/01101

§ 371 (c)(1),
(2), (4) Date: Oct. 10, 2003

(87) PCT Pub. No.: WO02/47603

PCT Pub. Date: Jun. 20, 2002

(65) Prior Publication Data

US 2004/0063711 A1    Apr. 1, 2004

(30) Foreign Application Priority Data

Dec. 15, 2000 (FI) .................... 20002755

(51) Int. Cl.
*A61K 31/50* (2006.01)
(52) U.S. Cl. ..................................... 514/247
(58) Field of Classification Search ................ 514/247
See application file for complete search history.

(56) References Cited

U.S. PATENT DOCUMENTS 5,565,466 A * 10/1996 Gioco et al. ................ 203/35
5,569,657 A * 10/1996 Nore et al. ................. 514/247

FOREIGN PATENT DOCUMENTS

| DE | 43 38 948 A1 | 5/1995 |
| EP | 0 565 546 B1 | 10/1993 |
| WO | WO 91/16052 | 10/1991 |
| WO | WO 92/12135 | 7/1992 |
| WO | WO 93/21921 | 11/1993 |
| WO | WO 98/01111 | 1/1998 |
| WO | WO 99/32081 | 1/1999 |
| WO | WO 99/21558 | 5/1999 |
| WO | WO 99/66912 | 12/1999 |

OTHER PUBLICATIONS

Gomaa et al., BMJ 1996; 312: 1512-1515.*
Stig Sundberg, Ph.D. et al., "Hemodynamic and Neurohumoral Effects of Levosimendan, a New Calcium Sensitizer, at Rest and During Exercise in Healthy Men", The American Journal of Cardiology, vol. 75, pp. 1061-1066, May 15, 1995.
J. Lilleberg et al., "Dose-Range Study of a New Calcium Sensitizer, Levosimendan, in Patients with Left Ventricular Dysfunction", Journal of Cardiovascular Pharmacology, 26 (Suppl. 1):S63-S69, 1995.
Esa-Pekka Sandell et al., "Pharmacokinetics of Levosimendan in Healthy Volunteers and Patients with Congestive Heart Failure", Journal of Cardiovascular Pharmacology, 26 (Suppl. 1):S57-S62, 1995.
J. Lilleberg et al., "Effects of a new calcium sensitizer, levosimendan, on haemodynamics, coronary blood flow and myocardial substrate utilization early after coronary artery bypass grafting", European Heart Journal (1998) 19, 660-668.
J.H. Naude et al., "Topical treatment of erectile dysfunction did not show results," BMJ, vol. 316, p. 1318 (1998).
Lue, "Erectile Dysfunction," The New Englsnd Journal of Medicine, vol. 342, pp. 1802-1813 (2000).

* cited by examiner

*Primary Examiner*—San-Ming Hui
(74) *Attorney, Agent, or Firm*—Finnegan, Henderson, Farabow, Garrett & Dunner, LLP

(57) ABSTRACT

Levosimendan, or (−)-[[4-(1,4,5,6-tetrahydro-4-methyl-6-oxo-3-pyridazinyl)phenyl]hydrazono]propanedinitrile, which has been previously suggested for the treatment of congestive heart failure, is useful in the treatment of erectile dysfunction.

4 Claims, No Drawings

METHOD FOR TREATING ERECTILE DYSFUNCTION

This application is a U.S. national stage filing of PCT International Application No. PCT/FI01/01101, filed on Dec. 14, 2001. This application also claims the benefit of priority under 35 U.S.C. § 119(a) to Finnish patent application no. 20002755, filed on Dec. 15, 2000.

TECHNICAL FIELD

The present invention relates to a method for the treatment of erectile dysfunction by administering levosimendan, or (−)-[[4-(1,4,5,6-tetrahydro-4-methyl-6-oxo-3-pyridazinyl)phenyl]hydrazono]propanedinitrile (I), or pharmaceutically acceptable salts thereof, to a patient in need of such treatment.

BACKGROUND OF THE INVENTION

Levosimendan, which is the (−)-enantiomer of [[4-(1,4,5,6-tetrahydro-4-methyl-6-oxo-3-pyridazinyl)phenyl]hydrazono]propanedinitrile, and the method for its preparation is described in EP 565546 B1. Levosimendan is potent in the treatment of heart failure and has significant calcium dependent binding to troponin. Levosimendan is represented by the formula:

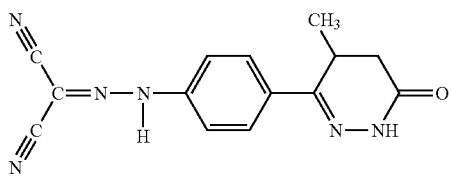

I

The hemodynamic effects of levosimendan in man are described in Sundberg, S. et al., Am. J. Cardiol., 1995; 75: 1061–1066 and in Lilleberg, J. et al., J. Cardiovasc. Pharmacol., 26(Suppl.1), S63–S69, 1995. Pharmacokinetics of levosimendan in man after i.v. and oral dosing is described in Sandell, E.-P. et al., J. Cardiovasc. Pharmacol., 26(Suppl.1), S57–S62, 1995. The use of levosimendan in the treatment of myocardial ischemia is described in WO 93/21921. The use of levosimendan in the treatment of pulmonary hypertension is described in WO 99/66912. Transdermal delivery of levosimendan is described in WO 98/01111. Transmucosal delivery of levosimendan is described in WO 99/32081. Clinical studies have confirmed the beneficial effects of levosimendan in heart failure patients.

Erectile dysfunction is the inability to obtain and sustain sufficient penile erection and is referred to as impotence. It can result from a variety of underlying causes ranging from purely psychogenic to completely physical dysfunctioning. Both surgical and pharmacological therapies have been used in the treatment of impotence.

SUMMARY OF THE INVENTION

It has now been found that levosimendan is capable of restoring or improving the erectile function in patients suffering from erectile dysfunction.

Therefore, the present invention provides the use of levosimendan or a pharmaceutically acceptable salt thereof in the manufacture of a medicament for the treatment of erectile dysfunction.

The present invention also provides a method for the treatment of erectile dysfunction in a patient, said method comprising administering to a patient in need thereof an effective amount of levosimendan or a pharmaceutically acceptable salt thereof.

DETAILED DESCRIPTION

The method of the invention comprises a step of administering to a subject an amount of levosimendan effective to restore the erectile function of the patient. The drug is preferably administered perorally, transmucosally including transurethrally, intravenously, intramuscularly including intracavernosal injection or transdermally. The administration may be systemic or local.

The effective amount of levosimendan to be administered to a subject depends upon the route of administration. Levosimendan is administered orally to man in daily dose from about 0.1 to 15 mg, preferably from about 0.5 to 10 mg, given once a day or divided into several doses a day. For transmucosal, intravenous, intramuscular or transdermal delivery the daily dose range is from about 0.005 to 0.7 mg/kg, preferably from about 0.01 to 0.5 mg/kg.

Levosimendan is formulated into dosage forms suitable for the treatment of erectile dysfunction using the principles known in the art. It is given to a patient as such or preferably in combination with suitable pharmaceutical excipients in the form of tablets, dragees, capsules, suppositories, emulsions, suspensions or solutions whereby the contents of the active compound in the formulation is from about 0.5 to 100% per weight. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds, release controlling components and other ingredients normally used in this field of technology may be also used.

For oral administration in tablet form, suitable carriers and excipients include e.g. lactose, corn starch, magnesium stearate, calcium phosphate and talc. For oral administration in capsule form, useful carriers and excipients include e.g. lactose, corn starch, magnesium stearate and talc. Disintegrants, such as croscarmellose sodium, may be used to accelerate the dissolution of the formulation.

Tablets can be prepared by mixing the active ingredient with the carriers and excipients and compressing the powdery mixture into tablets. Capsules can be prepared by mixing the active ingredient with the carriers and excipients and placing the powdery mixture in capsules, e.g. hard gelatin capsules. Typically a tablet or a capsule comprises from about 0.1 to 10 mg, more typically 0.2 to 5 mg, of levosimendan. In general, rapidly dissolving peroral tablets or capsules, e.g. having a dissintegration time of 1 to 20 minutes, are preferred.

Formulations suitable for intravenous administration such as injection formulation, comprise sterile isotonic solutions of levosimendan and vehicle, preferably aqueous solutions. Typically an intravenous infusion solution comprises from about 0.01 to 0.1 mg/ml of levosimendan.

Formulations of levosimendan suitable for transmucosal or transdermal administration are disclosed in WO 99/32081 and WO 98/01111, respectively.

Salts of levosimendan may be prepared by known methods. Pharmaceutically acceptable salts are useful as active medicaments, however, preferred salts are the salts with alkali or alkaline earth metals.

EXAMPLES

| Pharmaceutical example. Hard gelatin capsule size 3 | |
|---|---|
| Levosimendan | 2.0 mg |
| Lactose | 198 mg |

The pharmaceutical preparation in the form of a capsule was prepared by mixing levosimendan with lactose and placing the powdery mixture in hard gelatin capsule.

Clinical Data

Two NYHA III heart failure patients, who had not had erections for several years were treated with levosimendan. Patient I was exposed to 0.05 µg/kg/min continuous infusion of levosimendan for 7 days. The patient reported erections 1 day after starting the infusion and he had erections in the mornings during the whole study. Patient II reported erections after 0.1 µg/kg/min continuous infusion of levosimendan for 2 days.

The invention claimed is:

1. A method for the treatment of erectile dysfunction in a patient, said method comprising orally administering to a patient in need thereof an effective amount of levosimendan or a pharmaceutically acceptable salt thereof.

2. A method as claimed in claim 1, which comprises administering levosimendan or a pharmaceutically acceptable alkali or alkaline earth metal salt of levosimendan to the patient.

3. A method as claimed in claim 1, which comprises orally administering an effective amount of levosimendan to the patient.

4. A method as claimed in claim 1, which comprises orally administering an effective amount of a pharmaceutically acceptable salt of levosimendan to the patient.

* * * * *